United States Patent
Sutter et al.

(10) Patent No.: US 7,699,843 B2
(45) Date of Patent: Apr. 20, 2010

(54) INSTRUMENT FOR THE UNIPOLAR ABLATION OF HEART TISSUE

(75) Inventors: Bert Sutter, Emmendingen (DE); Guido Fehling, Karlstein (DE)

(73) Assignees: Fehling AG, Reinach (CH); Sutter Medizintechnik GmbH, Freiburg (DE)

( * ) Notice: Subject to any disclaimer, the term of this patent is extended or adjusted under 35 U.S.C. 154(b) by 849 days.

(21) Appl. No.: 10/558,442

(22) PCT Filed: May 19, 2004

(86) PCT No.: PCT/EP2004/005415

§ 371 (c)(1), (2), (4) Date: Sep. 12, 2006

(87) PCT Pub. No.: WO2004/103195

PCT Pub. Date: Dec. 2, 2004

(65) Prior Publication Data

US 2007/0043348 A1 Feb. 22, 2007

(30) Foreign Application Priority Data

May 26, 2003 (DE) .................. 103 23 566

(51) Int. Cl.
*A61B 18/18* (2006.01)
*A61B 18/12* (2006.01)

(52) U.S. Cl. .................. 606/41; 606/45; 607/101; 607/104

(58) Field of Classification Search ............ 606/41–48; 607/101–105
See application file for complete search history.

(56) References Cited

U.S. PATENT DOCUMENTS

| 4,919,129 | A | * | 4/1990 | Weber et al. ............... 606/42 |
| 5,250,047 | A | | 10/1993 | Rydell |
| 5,634,921 | A | * | 6/1997 | Hood et al. ................ 606/5 |
| 5,782,760 | A | | 7/1998 | Schaer |
| 5,944,715 | A | * | 8/1999 | Goble et al. ............... 606/41 |
| 6,053,172 | A | * | 4/2000 | Hovda et al. .............. 128/898 |
| 6,214,003 | B1 | | 4/2001 | Morgan et al. |
| 6,402,750 | B1 | * | 6/2002 | Atkinson et al. ........... 606/279 |
| 2001/0023347 | A1 | | 9/2001 | Sharkey et al. |
| 2003/0144656 | A1 | * | 7/2003 | Ocel et al. ................ 606/41 |

FOREIGN PATENT DOCUMENTS

| DE | 19713797 | 10/1997 |
| EP | 0697199 | 2/1996 |

* cited by examiner

*Primary Examiner*—Linda C Dvorak
*Assistant Examiner*—Benjamin Lee
(74) *Attorney, Agent, or Firm*—Akerman Senterfitt; Peter A. Chiabotti

(57) ABSTRACT

An instrument for the unipolar ablation of heart tissue comprises: an electrically conductive shaft tube (20) that is electrically insulated on the outer lateral surface; an electrical connection, which is placed at the proximal end of the shaft tube (20) and which is connected to the shaft tube (20) in a conductive manner; a flushing connection, which is situated at the proximal end of the shaft tube (20) and which communicates with the bore of the shaft tube (20), and; an electrode (14), which is inserted into the distal end of the shaft tube (20), is connected to the shaft tube (20) in an electrically conductive manner, and which has at least one discharge opening (34) that communicates with the bore of the shaft tube (20). The electrode (14) is detachably connected to the distal end of the shaft tube (20).

16 Claims, 2 Drawing Sheets

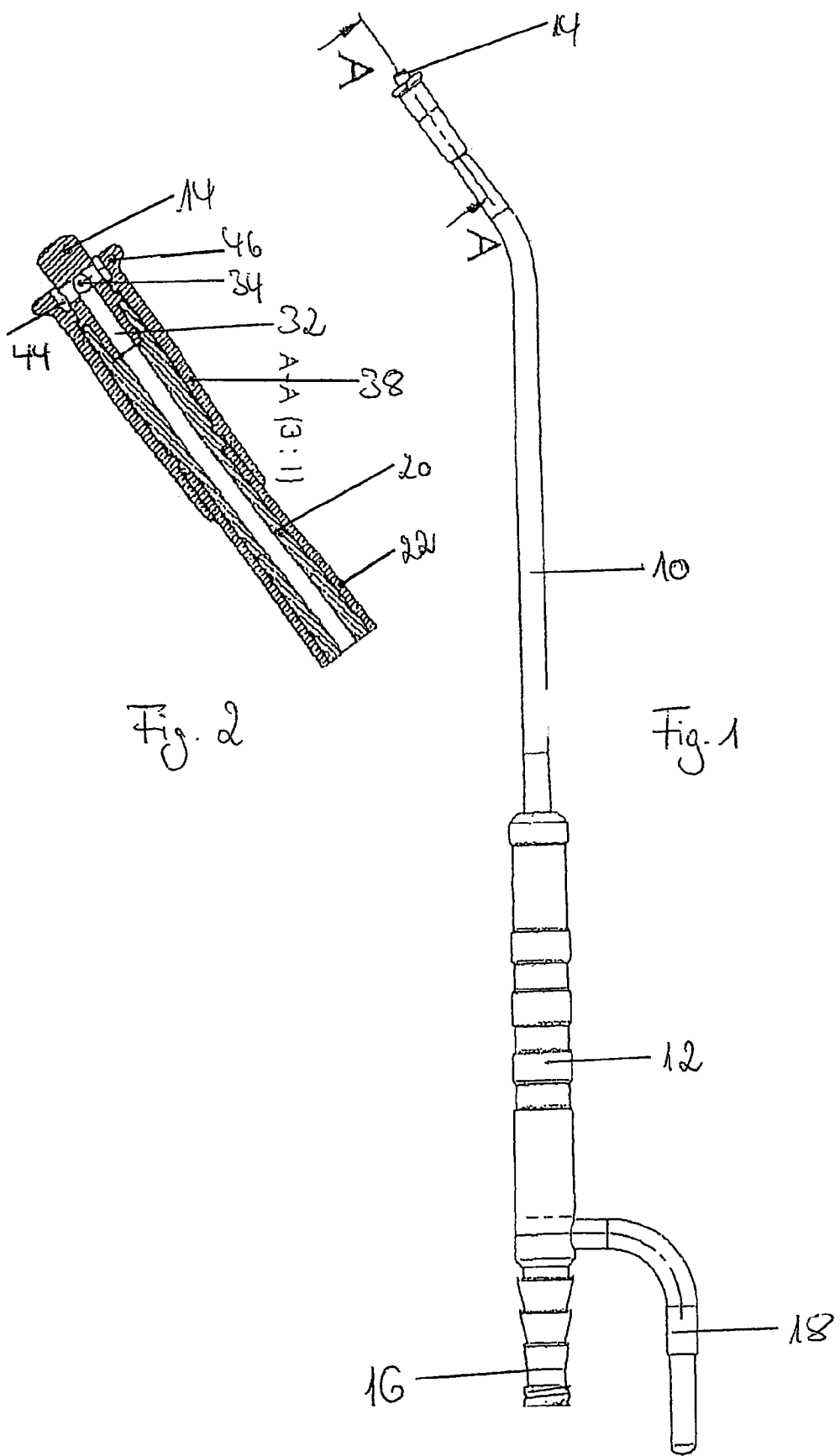

INSTRUMENT FOR THE UNIPOLAR ABLATION OF HEART TISSUE

CROSS REFERENCE TO RELATED APPLICATION

This application is a national stage of PCT/EP2004/005415 filed May 19, 2004 and based upon DE 103 23 566.3 filed May 26, 2003 under the International Convention.

BACKGROUND OF THE INVENTION

1. Field of the Invention

The invention relates to an instrument for the unipolar ablation of heart tissue.

2. Related Art of the Invention

In surgical heart therapy electrical ablation is utilized, e.g. for the treatment of arrhythmia. Electrical energy, preferably in form of high frequency current is conducted into the region of the heart tissue causing the arrhythmia, particularly the atrium, to selectively damage the tissue in order to eliminate the cause of the arrhythmia. For this, instruments with bipolar and with unipolar supply of HF-energy are known. Further, it is known that a rinsing liquid may flow through the instrument and be discharged at the distal end in the region of the electrode. The rinsing liquid, e.g. a Ringer solution or other electrolytic liquid, serves for cooling and, as the case may be, for improvement of the electrical conductivity between the electrode and the tissue.

In U.S. Pat. No. 5,782,760 an instrument of the previously mentioned kind is disclosed. This instrument is introduced into the heart of the patient through a blood vessel. Here the tube, which conducts the electrical energy and the rinsing liquid to the distal end, is constituted as a flexible catheter. In instruments which are introduced by means of an invasive surgical intervention through the thorax into the heart, the tube is constituted as a rigid shaft.

SUMMARY OF THE INVENTION

The objective of the invention is to create an instrument of the above mentioned kind which is cost efficient and ergonomically advantageous.

The instrument for the unipolar ablation of heart tissue according to the invention is introduced through the opened thorax or a micro invasive cut into the atrium of the heart. The instrument features a rigid shaft tube which carries on its distal end a detachable electrode. The shaft tube with its handle on the proximal end, the proximal electrical connection and the proximal connection for the rinsing liquid is designed as a re-usable part which can be disinfected and sterilized repetitively. The electrode is easily exchangeable, preferably via a plug-in connection, so that the electrode can be constructed as a single-use disposable. Thus the instrument is cost efficient for this use.

In an especially advantageous embodiment the electrode is snapped onto the distal end of the shaft tube by means of a detent, providing for a simple exchange of the electrode without the necessity for special tools or special technical knowledge.

The handle preferably consists of plastic and is molded directly onto the proximal end of the shaft tube, which on one hand provides an ergonomically advantageous handling of the instrument and on the other hand results in a reduction of the production cost.

BRIEF DESCRIPTION OF THE DRAWINGS

An advantageous embodiment of the invention will be described in detail in the examples below. They show:
FIG. 1 an overall view of the instrument,
FIG. 2 the distal end of the instrument in an axial cross-section along the line A-A in FIG. 1,
FIG. 3 the distal end of the shaft tube in axial cross-section,
FIG. 4 the distal electrode in a side view and
FIG. 5 an electrode ferrule in axial cross-section.

DETAILED DESCRIPTION OF THE INVENTION

Figures 3, 4, 5:
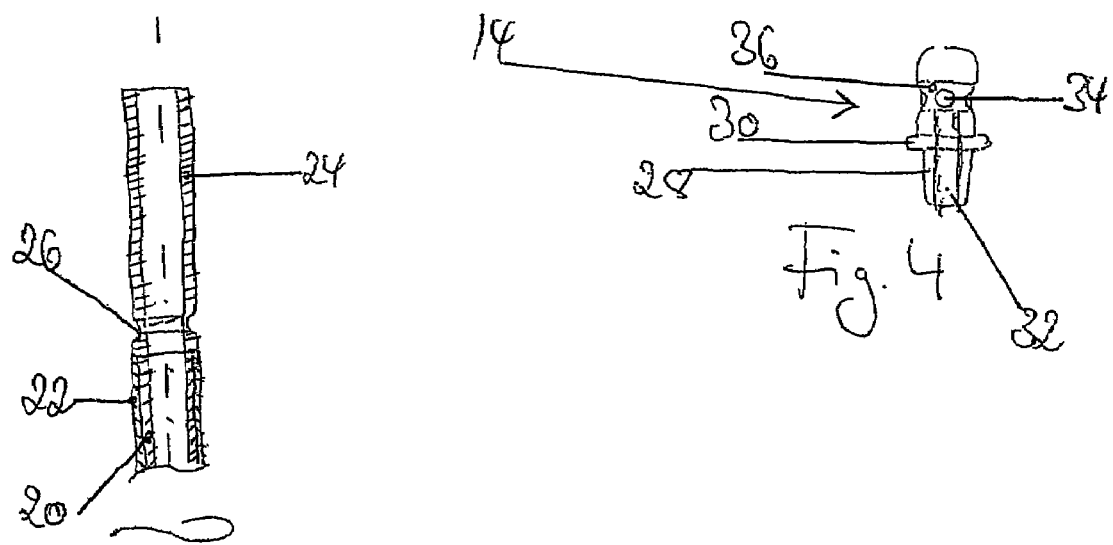

FIG. 1 shows the overall instrument for the unipolar ablation of heart tissue approximately in a 1:1 scale. The instrument features a shaft 10 with a handle 12 on its proximal end. On the distal end of the shaft 10 an electrode 14 is located. At the proximal end of the handle 12 a rinse connection 16 is located axially aligned along the centerline of the shaft 10 which is constituted as a hose connection to connect to a hose for the rinsing fluid. Also at the proximal end is an electric connection 18 which is preferably constituted as a plug and socket connection for the high frequency power supply.

The handle 12 encloses the shaft 10 cylindrically like a penholder handle. The distal end of the shaft 10 with the electrode 14 is angled between approximately 30° and 45° with respect to the centerline of the shaft 10. Thus, it provides for ergonomic handling and enables unerring placement of the electrode tip.

The shaft 10 is constituted by an electrically conducting rigid metallic shaft tube 20 which over its entire length is covered by an electrically insulating cladding 22 made from plastic. The handle 12 preferably consists of the same plastic material such that the handle 12 can be molded around the shaft tube 20 as one piece together with the cladding 22.

The construction of the distal end of the instrument is shown in detail in FIGS. 2 through 3.

As shown in FIGS. 2 and 3 the insulating cladding 22 ends before the distal end of the shaft tube 20, so that a distal end section 24 of the shaft tube 20 remains uncovered by the cladding 22. In this end section 24 directly in front of the distal end of the cladding 22 a radial groove 26 is machined into the outer circumflex of the shaft tube 20.

As shown in FIGS. 2 and 4 the electrode 14 is constituted by an essentially cylindrical body made of an electrically conducting material. The electrode 14 is pushed with its proximal end section 28 into the distal end of the shaft tube 20, in which the outer diameter of said end section 28 equals the inner diameter of the shaft tube 20, such that the electrode 14 can be introduced into the shaft tube 20 with a tight fit. The electrode 14 is stopped with its external collar 30 on the distal end of the shaft tube 20. The outer diameter of the external collar equals essentially the outer diameter of the end section 24 of the shaft tube 20. The distal end of the electrode 14 which constitutes the distal end of the instrument is monolithic and domed in distal direction. From the proximal end a blind hole 32 coaxially leads into the electrode 14. The blind hole 32 stretches in distal direction beyond the external collar 30. At the distal end of the blind hole 32 four discharge openings 34 with an offset of 90° to each other stretch radially from the circumflex of the electrode 14 into the blind hole 32. The discharge openings 34 meet at their outer end with a shared circumferential recess 36 of the electrode 14.

As shown in FIGS. 2 and 5 an electrode ferrule 38 made of electrically insulating plastic is pushed from the distal end over the electrode 14 which sits in the shaft tube 20. When assembled (FIG. 2) the electrode ferrule 38 axially overlaps with its proximal end the distal end of the insulating cladding 22. Thus the electrode ferrule 38 seamlessly continues the electrical insulation of the cladding 22. The electrode ferrule 38 features in its proximal end region an internal detent 40 which snaps into the radial groove 26 of the shaft tube 20 when the electrode ferrule 38 is assembled. The detent 40 may be constituted from a single punctiform cam, multiple angled and staggered cams or a bead covering a pitch circle.

In the distal end section the electrode ferrule 38 features an internal collar 42. When the electrode ferrule 38 is assembled, the internal collar 42 axially contacts and stops at the external collar 30 of the electrode 14 whereby the electrode 14 is fixed in the distal end of the shaft tube 20 and the electrode 14, by means of its external collar 30, maintains an electrically conducting path to the distal end of the shaft tube 20. Thus a reliable electrical contact between the shaft tube 20 and the electrode 14 is guaranteed. At the distal end of the electrode ferrule 38, before the internal collar 42, the inner diameter of the electrode ferrule 38 is larger than the outer diameter of the electrode 14, so that between the electrode 14 and the electrode ferrule 38 an annular gap 44 remains open in the distal direction. The discharge openings 34 meet with this annular gap 44. The electrode ferrule 38 which is pushed and snapped onto the shaft tube 20 ends distally in a radially enlarged flange 46. The distal end of the electrode 14 protrudes the flange 46 in the distal direction, so that the flange 46 serves as a stop, limiting the insertion depth of the tip of the electrode 14 into the tissue being treated.

The proximal electrical connection 18 of the instrument is connected to a high frequency power supply which is not shown. The high frequency current flows from the electrical connection 18 through the shaft tube 20 to the electrode 14. With the electrode's 14 bare distal tip the unipolar current is applied to the treated tissue. With exception of the bare electrode tip, the shaft tube 20 and the electrode 14 are completely electrically insulated on their outside through the handle 12, the cladding 22 and the electrode ferrule 38.

Through the proximal rinse connection 16 a rinsing liquid is introduced. The rinsing liquid flows through the lumen of the shaft tube 20 into the blind hole 32 of the electrode 14 and escapes through the radial discharge openings 34. Through the circumferential recess 36 and the annular gap 44 a uniform flow around the tip of the electrode 14 is achieved.

REFERENCE NUMERAL LIST

| 10 | shaft |
|---|---|
| 12 | handle |
| 14 | electrode |
| 16 | rinse connection |
| 18 | electric connection |
| 20 | shaft tube |
| 22 | cladding |
| 24 | end section of 20 |
| 26 | radial groove |
| 28 | proximal end section of 14 |
| 30 | external collar of 14 |
| 32 | blind hole |
| 34 | discharge opening |
| 36 | circumferential recess |
| 38 | electrode ferrule |
| 40 | detent |
| 42 | internal collar |
| 44 | annular gap |
| 46 | flange |

We claim:

1. An instrument for the unipolar ablation of heart tissue, comprising:
    an electrically conductive tube electrically insulated on its outer surface, with an electrical connector on a proximal end of the tube which is electrically conductively connected to said tube, with a rinse connection on the proximal end of the tube which is in communication with a lumen of the tube and an electrode mounted into a distal end of the tube which is connected electrically conductively to the tube and which features at least one discharge opening which is in communication with the lumen of the tube, wherein the tube is a shaft tube and that the electrode is connected detachably with the distal end of the shaft tube; and
    wherein the electrode is coaxially inserted into the distal end of the shaft tube axially contacting a stop establishing an electrical contact with the shaft tube and wherein that an electrically insulating electrode ferrule which surrounds the electrode is snapped onto the shaft tube and holds the electrode in a stop position on the shaft tube.

2. An instrument according to claim 1, wherein the electrode is connected to the shaft tube by means of an axial plug-in detent.

3. An instrument according to claim 1, wherein the electrode ferrule coaxially overlaps an insulating cladding of the shaft tube in part and snaps on by means of a radial groove and a corresponding detent.

4. An instrument according to claim 1, wherein the electrode inserted coaxially into the distal end of the shaft tube contacts the distal end of the shaft tube axially with its external collar.

5. An instrument according to claim 4, wherein the electrode ferrule features an internal collar which distally contacts the external collar of the electrode and which secures the electrode axially contacting to the shaft tube.

6. An instrument according to claim 1, wherein between the outer surface of the electrode and a distal end of the electrode ferrule an annular gap remains open in a distal direction, and wherein at least one discharge opening meets with this annular gap.

7. An instrument according to claim 1, wherein a handle made from plastic is located at the proximal end of the shaft tube.

8. An instrument according to claim 7, wherein the handle is in a form of a pen grip and is directly molded onto the shaft tube.

9. An instrument according to claim 7, wherein the handle and a cladding of the shaft tube consist of a same material.

10. An instrument according to claim 1, wherein the distal end of the shaft tube with the electrode is angled between approximately 30° and 45° with respect to a centerline of the shaft tube.

11. An instrument according to claim 1, and wherein the electrode ferrule features a radially enlarged flange on its distal end which limits an insertion depth of a tip of the electrode which protrudes from the flange in a distal direction.

12. An instrument for the unipolar ablation of heart tissue, comprising:
    an electrically conductive tube electrically insulated on its outer surface, with an electrical connector on a proximal end of the tube which is electrically conductively connected to said tube, with a rinse connection on the proximal end of the tube which is in communication with a lumen of the tube and an electrode mounted into a distal end of the tube which is connected electrically conductively to the tube and which features at least one discharge opening which is in communication with the lumen of the tube, wherein the tube is a shaft tube and that the electrode is connected detachably with the distal end of the shaft tube;

wherein the electrode is constituted as a cylindrical part closing the lumen of the shaft tube which features a proximal blind hole which is open to the lumen of the shaft tube in which at least one radial discharge opening extends radially from a circumflex of the electrode into the blind hole; and wherein an electrically insulating electrode ferrule which surrounds the electrode is snapped onto the shaft tube and holds the electrode in a stop position on the shaft tube, wherein between the outer surface of the electrode and a distal end of the electrode ferrule an annular gap remains open in a distal direction, and wherein at least one discharge opening meets with this annular gap.

13. An instrument according to claim 12, wherein the electrode is coaxially inserted into the distal end of the shaft tube axially contacting a stop establishing the electrical contact with the shaft tube.

14. An instrument according to claim 12, and wherein the electrode ferrule features a radially enlarged flange on its distal end which limits a insertion depth of a tip of the electrode which protrudes from the flange in a distal direction.

15. An instrument for the unipolar ablation of heart tissue, comprising:
   an electrically conductive tube electrically insulated on its outer surface, with an electrical connector on a proximal end of the tube which is electrically conductively connected to said tube, with a rinse connection on the proximal end of the tube which is in communication with a lumen of the tube and an electrode mounted into a distal end of the tube which is connected electrically conductively to the tube and which features at least one discharge opening which is in communication with the lumen of the tube, wherein the tube is a shaft tube and that the electrode is connected detachably with the distal end of the shaft tube; and
   wherein an electrically insulating electrode ferrule which surrounds the electrode is snapped onto the shaft tube and holds the electrode in a stop position on the shaft tube, and wherein the electrode ferrule features a radially enlarged flange on its distal end which limits an insertion depth of a tip of the electrode which protrudes from the flange in a distal direction.

16. An instrument according to claim 15, wherein the electrode is coaxially inserted into the distal end of the shaft tube axially contacting a stop establishing an electrical contact with the shaft tube.

* * * * *